United States Patent
Matsuo

(10) Patent No.: US 10,052,039 B2
(45) Date of Patent: *Aug. 21, 2018

(54) LIGHT DETECTION UNIT

(71) Applicant: Seiko Epson Corporation, Tokyo (JP)

(72) Inventor: Atsushi Matsuo, Azumino (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/112,237

(22) PCT Filed: Mar. 10, 2015

(86) PCT No.: PCT/JP2015/001311
§ 371 (c)(1),
(2) Date: Jul. 18, 2016

(87) PCT Pub. No.: WO2015/141184
PCT Pub. Date: Sep. 24, 2015

(65) Prior Publication Data
US 2016/0331252 A1 Nov. 17, 2016

(30) Foreign Application Priority Data
Mar. 18, 2014 (JP) ................................. 2014-054722

(51) Int. Cl.
*A61B 5/024* (2006.01)
*A61B 5/00* (2006.01)

(52) U.S. Cl.
CPC .......... *A61B 5/02427* (2013.01); *A61B 5/002* (2013.01); *A61B 5/459* (2013.01);
(Continued)

(58) Field of Classification Search
CPC ..... A61B 5/02427; A61B 5/002; A61B 5/459; A61B 5/4866; A61B 5/6803; A61B 5/681; A61B 5/6824; A61B 5/721; A61B 5/7455
See application file for complete search history.

(56) References Cited

U.S. PATENT DOCUMENTS

| | | | | |
|---|---|---|---|---|
| 4,685,464 A | * | 8/1987 | Goldberger | ........ A61B 5/14552 600/344 |
| 8,740,791 B2 | * | 6/2014 | Sato | ................... A61B 5/02427 324/502 |

(Continued)

FOREIGN PATENT DOCUMENTS

| JP | 6-273229 A | 9/1994 |
|---|---|---|
| JP | 6-042396 U | 11/1994 |

(Continued)

OTHER PUBLICATIONS

Search Report received in International Application No. PCT/JP2015/001311, dated Jun. 2, 2015.

(Continued)

*Primary Examiner* — Catherine Voorhees
(74) *Attorney, Agent, or Firm* — ALG Intellectual Property, LLC

(57) ABSTRACT

A light detection unit includes a light emitter that emits light toward an object of interest, a light receiver that receives light from the object of interest, and a light blocking member that performs light blocking at least above the light receiver. The light blocking member includes a first surface that is provided between the light emitter and the light receiver and prevents direct light from the light emitter from entering the light receiver and a second surface and a third surface that are provided along a direction that intersects the first surface and prevent light from entering the light receiver. Further, the first surface is made of a first material, and the second (Continued)

surface and the third surface are made of a second material different from the first material.

12 Claims, 10 Drawing Sheets

(52) U.S. Cl.
CPC ............ *A61B 5/4866* (2013.01); *A61B 5/681* (2013.01); *A61B 5/6803* (2013.01); *A61B 5/6824* (2013.01); *A61B 5/721* (2013.01); *A61B 5/7455* (2013.01)

(56) References Cited

U.S. PATENT DOCUMENTS

| | | |
|---|---|---|
| 2008/0219673 A1 | 9/2008 | Goh et al. |
| 2010/0032716 A1 | 2/2010 | Sato et al. |
| 2011/0121181 A1 | 5/2011 | Costello et al. |
| 2011/0260176 A1 | 10/2011 | Onoe et al. |
| 2012/0176599 A1 | 7/2012 | Leung et al. |
| 2013/0019459 A1 | 1/2013 | Lim et al. |
| 2013/0187891 A1* | 7/2013 | Eriksson ............... G06F 3/0421 345/175 |
| 2013/0267273 A1* | 10/2013 | Rudmann ............. G01S 17/026 455/556.1 |
| 2013/0292706 A1* | 11/2013 | Costello ................ H01L 31/167 257/82 |
| 2014/0103199 A1 | 4/2014 | Loong et al. |
| 2014/0228690 A1 | 8/2014 | Sato et al. |
| 2016/0120421 A1* | 5/2016 | Matsuo .............. A61B 5/02055 600/476 |

FOREIGN PATENT DOCUMENTS

| | | | |
|---|---|---|---|
| JP | 2004-061482 A | | 2/2004 |
| JP | 2007-175415 A | | 7/2007 |
| JP | 2009-168670 A | | 7/2009 |
| JP | 2009168670 A | * | 7/2009 |
| JP | 2009-201919 A | | 9/2009 |
| JP | 2010-200970 A | | 9/2010 |
| JP | 2011-139725 A | | 7/2011 |

OTHER PUBLICATIONS

Extended European Search Report received in EP Application No. 15764499 dated Nov. 2, 2017.

\* cited by examiner

[Fig. 1]
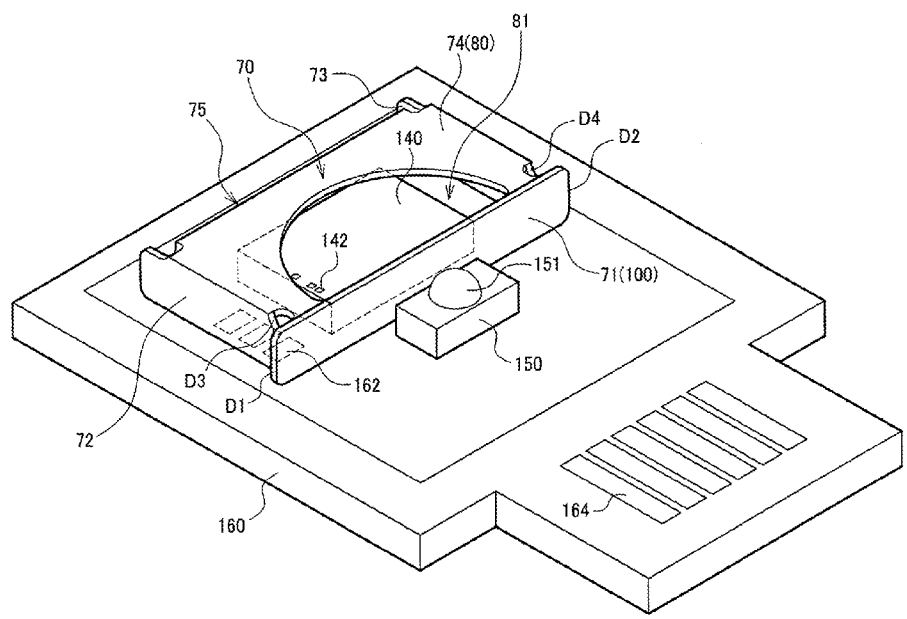
[Fig. 2A]
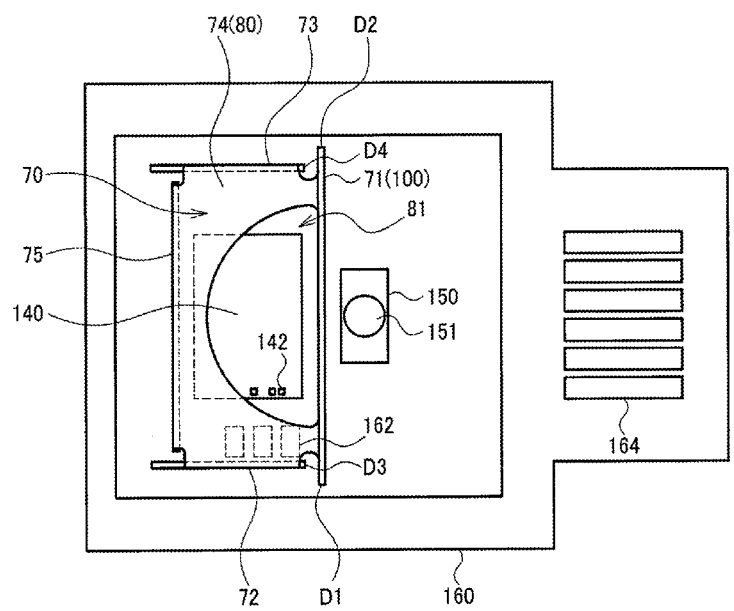

[Fig. 2B]
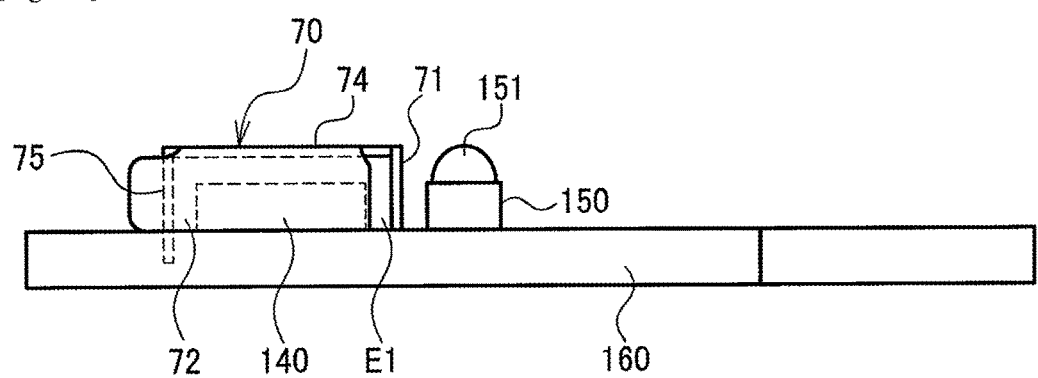

[Fig. 3]
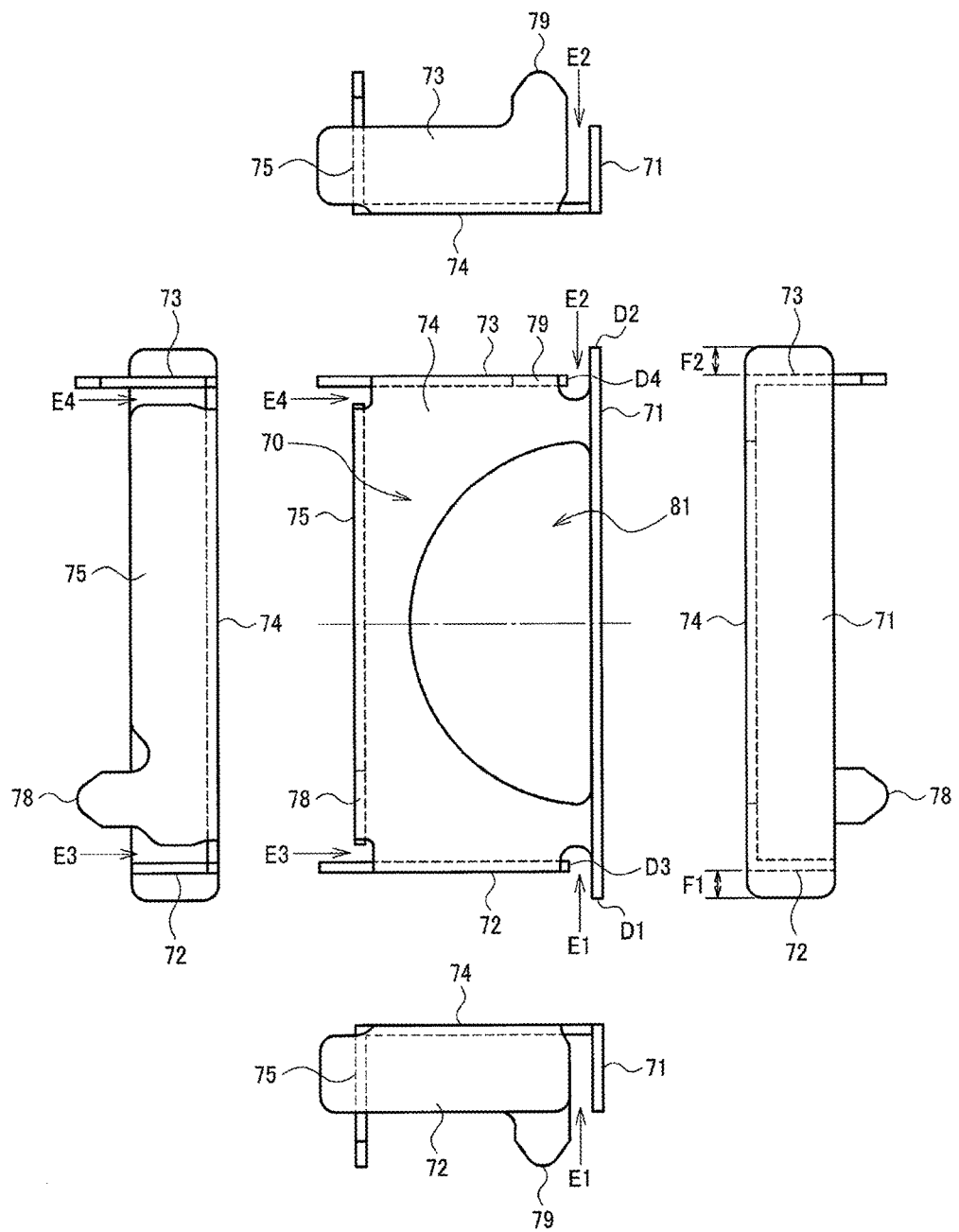

[Fig. 4]
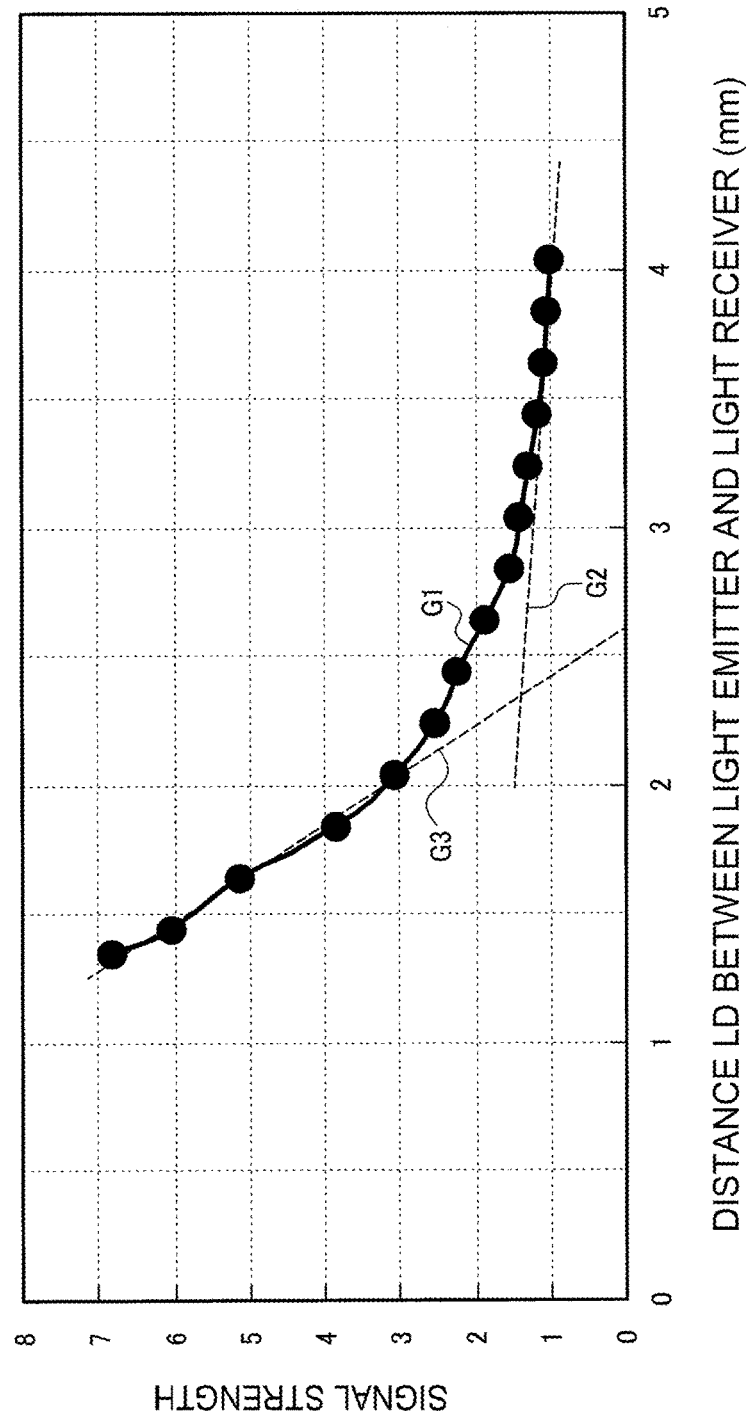

[Fig. 5]
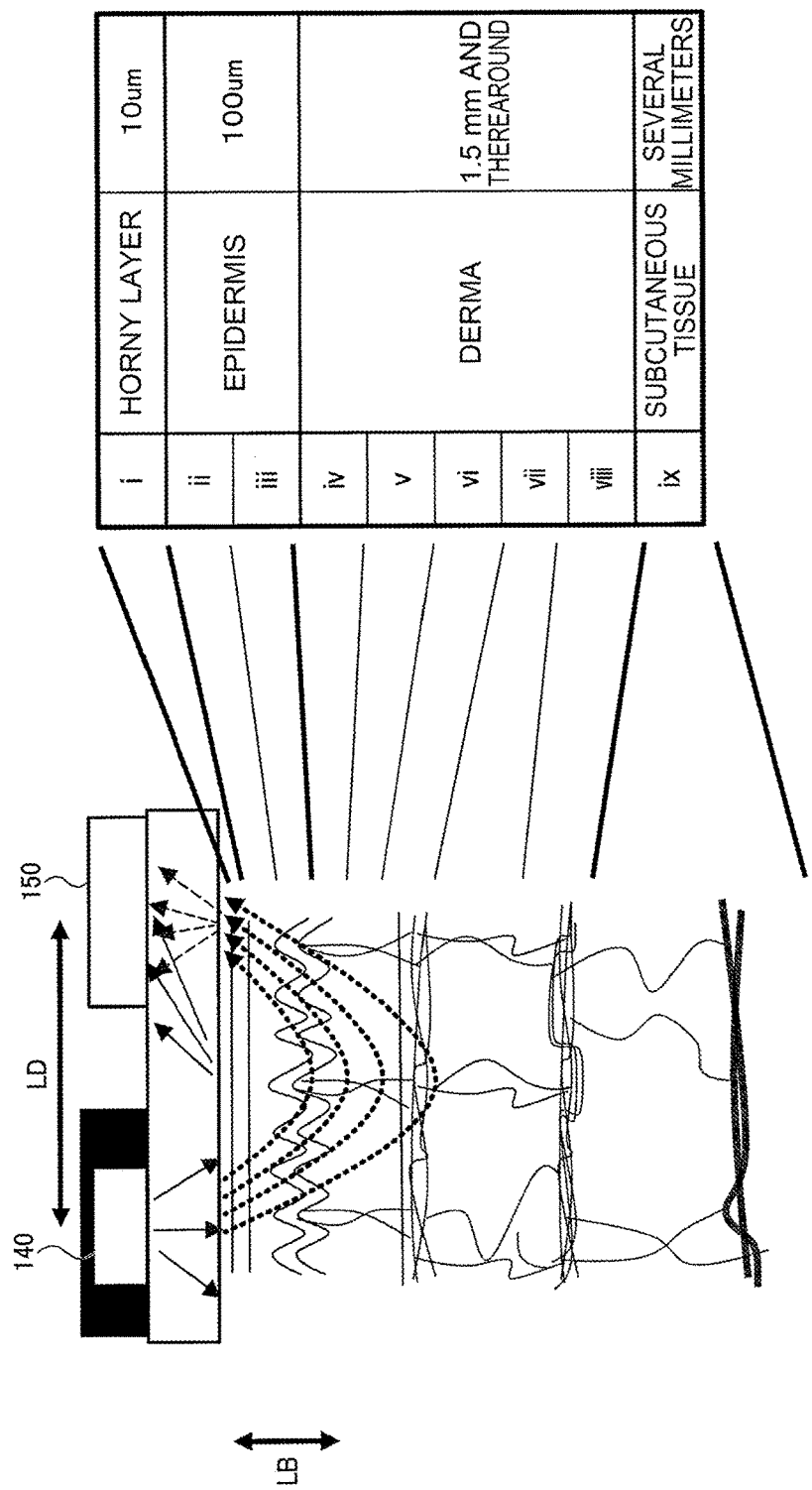

[Fig. 6A]
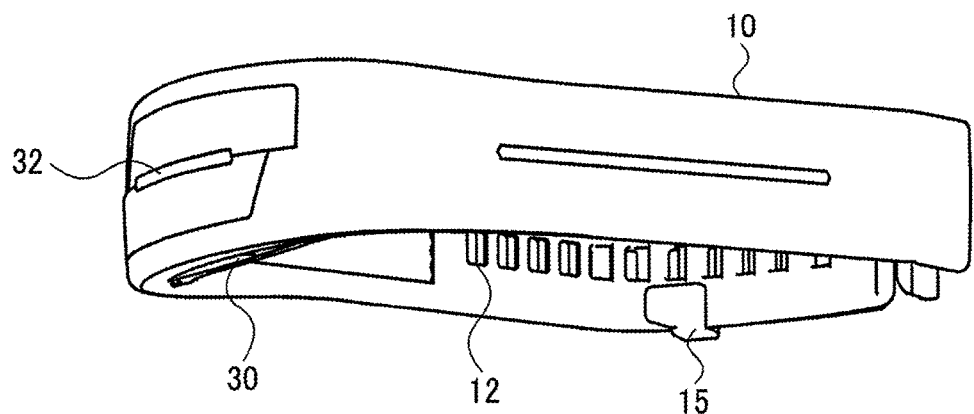
[Fig. 6B]
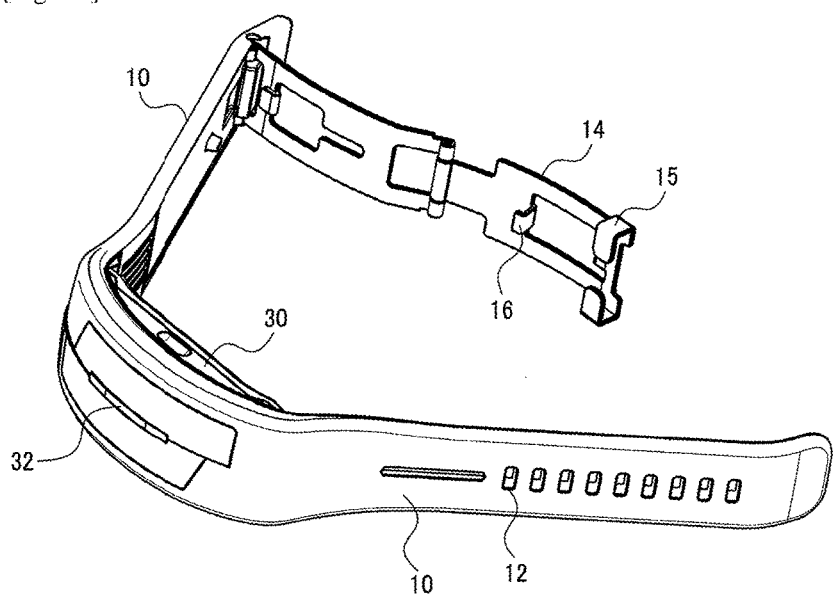

[Fig. 7]
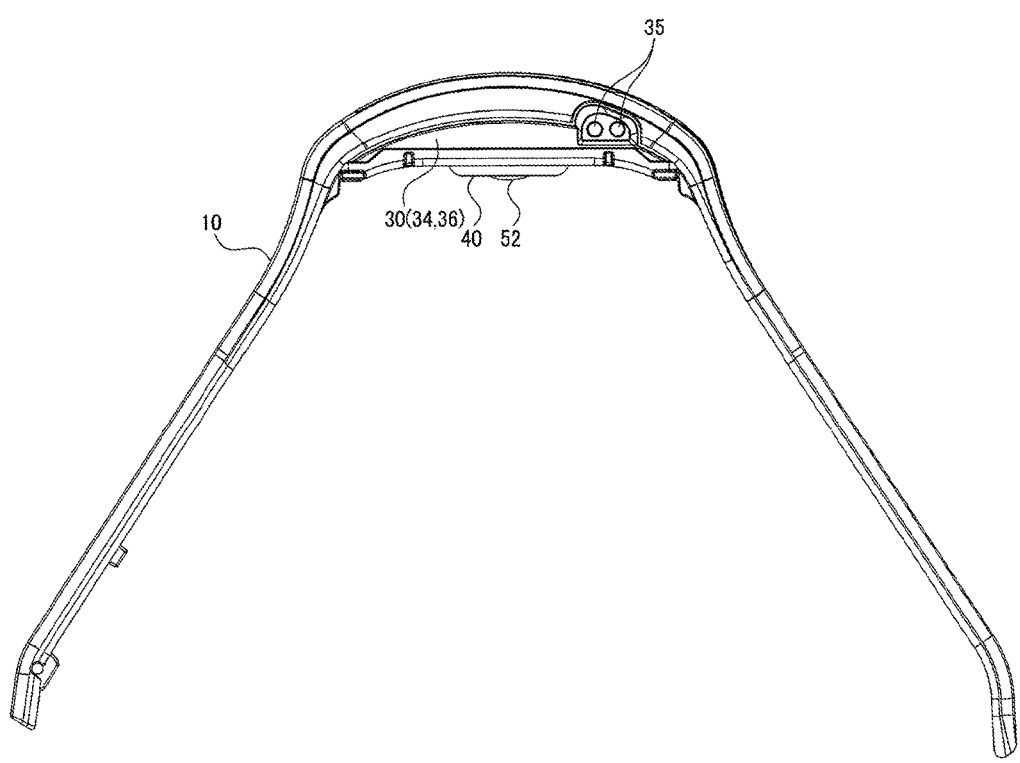

[Fig. 8]
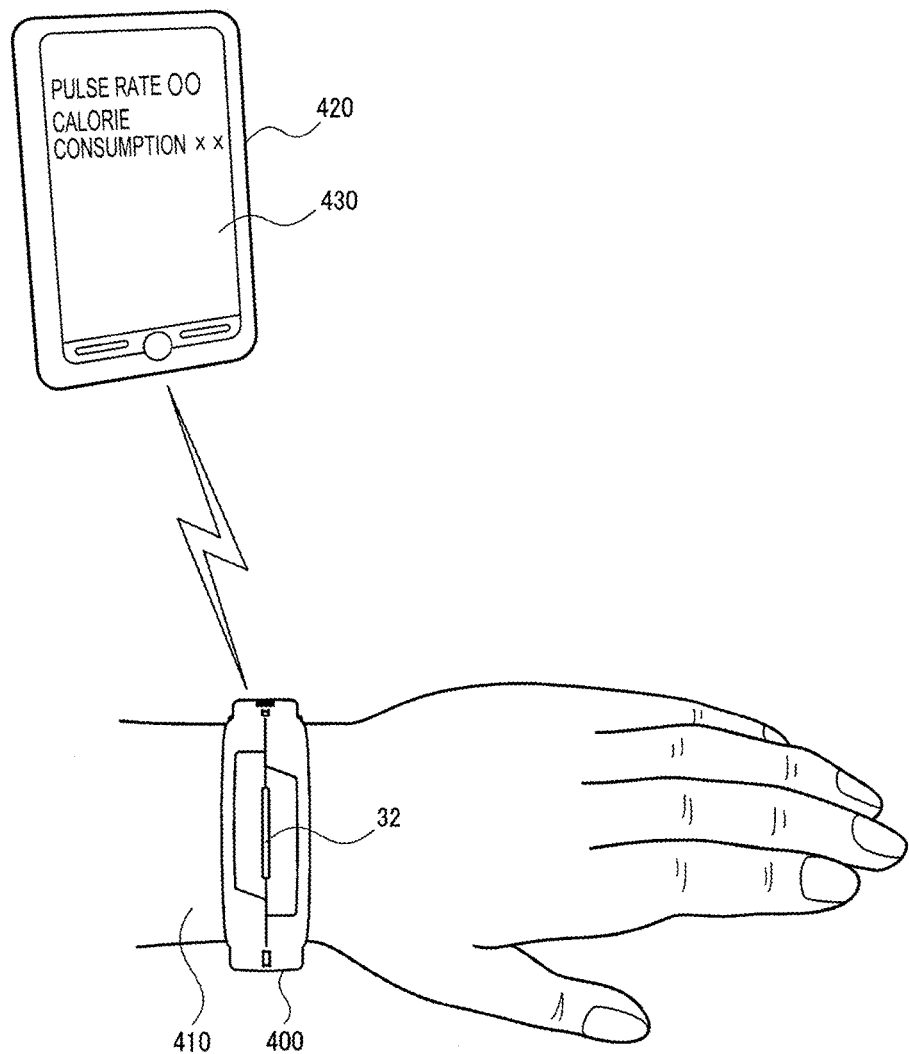

[Fig. 9]
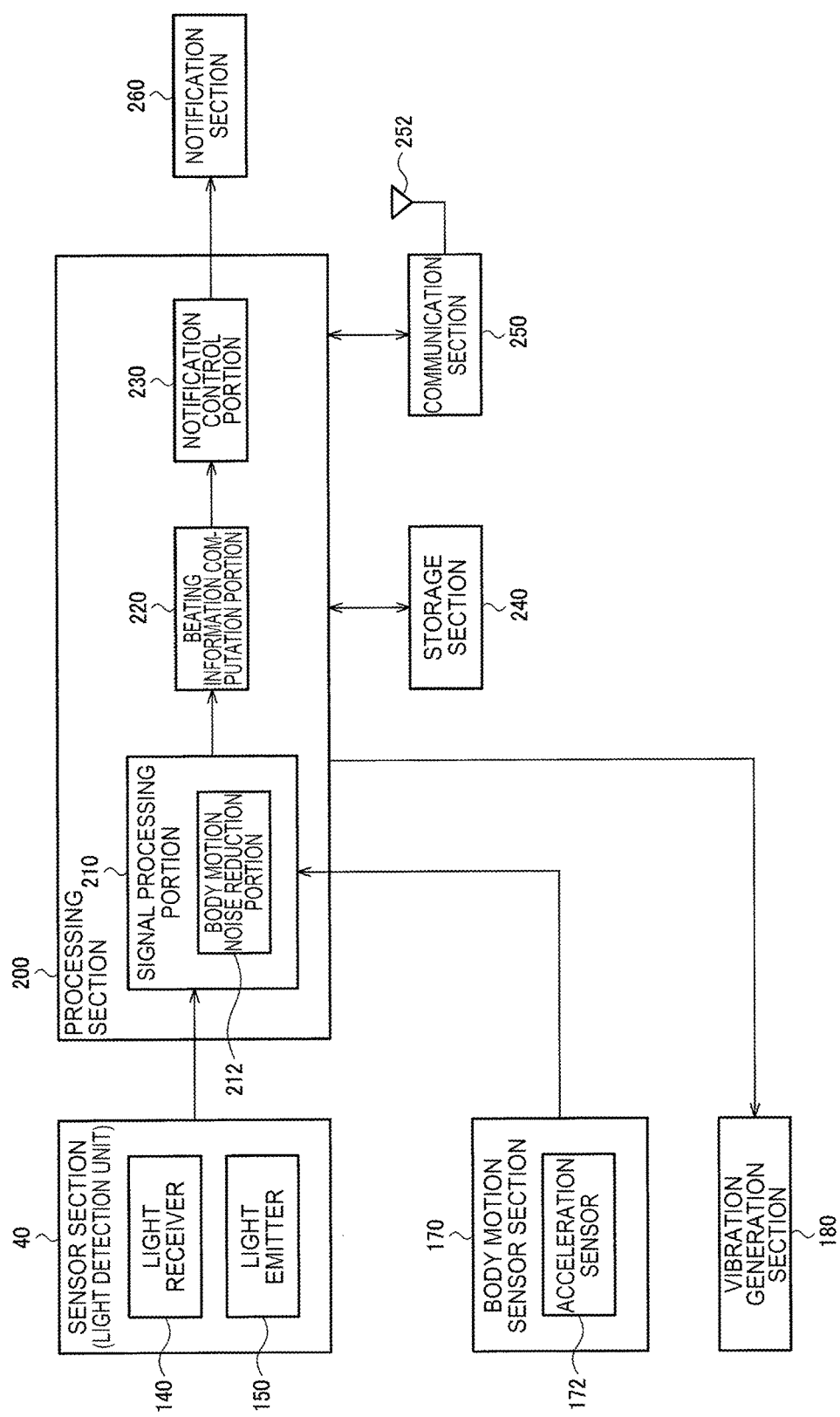

[Fig. 10A]
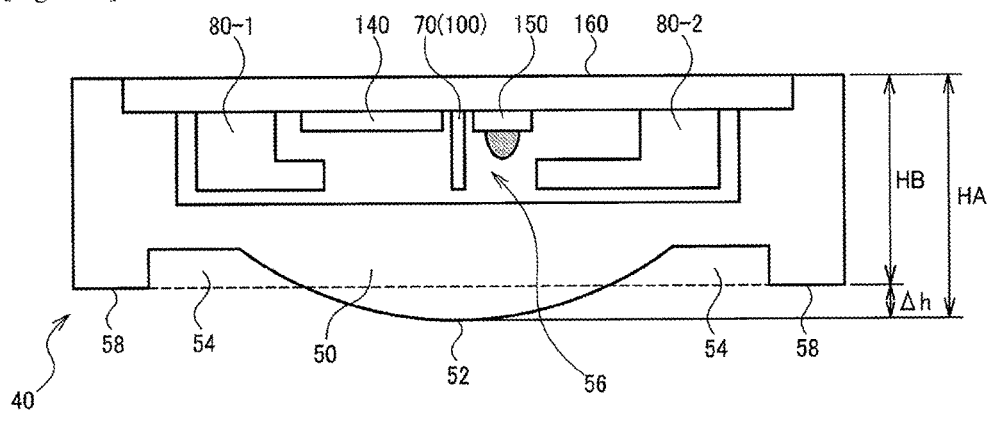
[Fig. 10B]
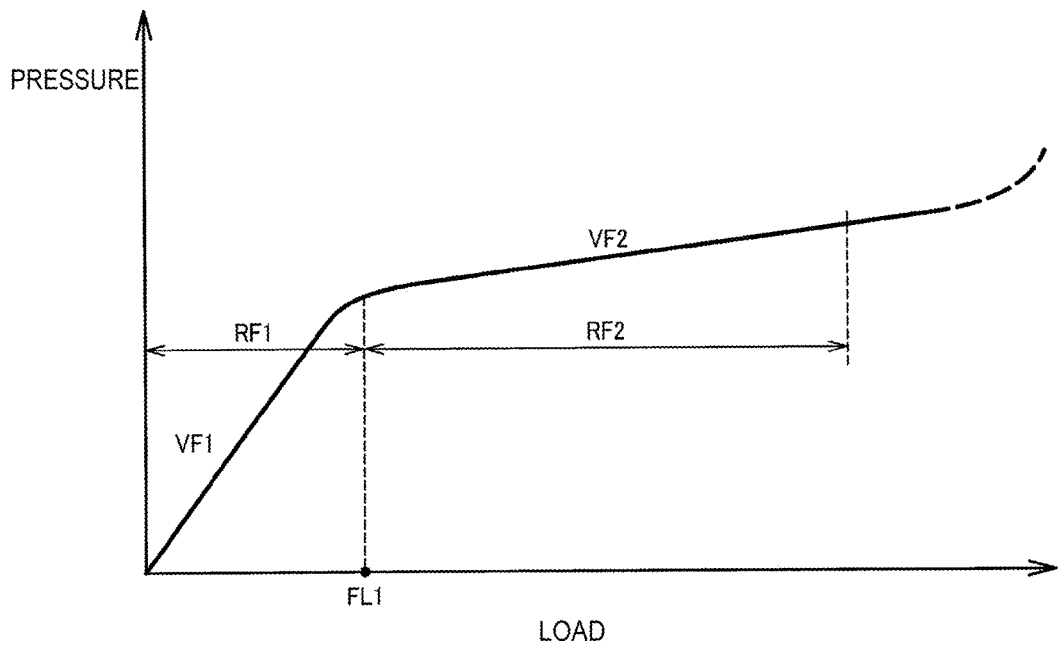

LIGHT DETECTION UNIT

TECHNICAL FIELD

The present invention relates to a light detection unit and the like.

BACKGROUND ART

There is a known biological information detection apparatus that detects biological information, such as a pulse wave of a person. PTL 1 and PTL 2 each disclose related art of a pulse rate meter, which is an example of the biological information detection apparatus. The pulse rate meter is worn, for example, around an arm, a wrist, a finger, or any other portion of a human body and detects beating resulting from the heartbeat of the human body to measure the pulse rate.

Each of the pulse rate meters disclosed in PTL 1 and PTL 2 is a photoelectric pulse rate meter, and a light detection unit thereof includes a light emitter that emits light toward a subject that is an object of interest and a light receiver that receives light from the subject (light containing biological information). The pulse rate meter detects a change in the amount of blood flow in the form of a change in the amount of received light to detect a pulse wave. PTL 1 discloses a pulse rate meter of a type worn around a wrist, and PTL 2 discloses a pulse rate meter of a type worn around a finger. Further, PTL 3 discloses a light sensor including a light receiver provided with a light blocking member.

CITATION LIST

Patent Literature

PTL 1: JP-A-2011-139725
PTL 2: JP-A-2009-201919
PTL 3: JP-A-6-273229

SUMMARY OF INVENTION

Technical Problem

In an apparatus of the type described above that detects biological information and the like, the light emitter in the light detection unit of the apparatus emits light toward an object of interest, and a variety of types of information are detected based on a detection signal produced by the light receiver that receives light from the object of interest. Improvement in the quality of the detection signal is therefore an important issue. For example, if the light from the light emitter enters the light receiver, reliability, detection accuracy, and other factors of detected information can undesirably decrease.

Solution to Problem

An advantage of some aspects of the invention is to provide a light detection unit and the like capable of improving detection performance while preventing light from a light emitter from entering a light receiver.

An aspect of the invention relates to a light detection unit including a light emitter that emits light toward an object of interest, a light receiver that receives light from the object of interest, and a light blocking member that performs light blocking at least on or above the light receiver. The light blocking member includes a first surface that is provided between the light emitter and the light receiver and prevents direct light from the light emitter from entering the light receiver and a second surface and a third surface that are provided along a direction that intersects the first surface and prevent light from entering the light receiver. The first surface is made of a first material, and the second surface and the third surface are made of a second material different from the first material.

According to the aspect of the invention, the light emitter emits light toward an object of interest, and light from the object of interest is received by the light receiver. The light blocking member is so provided that it performs light blocking at least on or above the light receiver. Configuring the light blocking member to have the first surface made of the first material prevents the light from the light emitter from entering the light receiver, whereby the detection performance and the like of the light detection unit can be improved. Further, forming the second surface and the third surface with the second material different from the first material of the first surface allows each of the second surface and the third surface to be made of an optimum material.

In the aspect of the invention, the first material may be a metal material, and the second material may be a material other than the metal material.

Forming the first surface with a metal material as described above, for example, allows formation of a thin first surface and therefore readily allows the distance between the light emitter and the light receiver to be shortened. As a result, the detection performance and the like of the light detection unit can be improved with the light from the light emitter not allowed to enter the light receiver.

Further, the second surface and the third surface can, for example, instead be directly formed of an enclosure (case) of the light detection unit or formed of any other part that forms the light detection unit. The second surface and the third surface can thus, for example, be manufactured at a reduced cost.

In the aspect of the invention, the first surface may be a metal plate formed in sheet metal working.

A metal plate excels in light blocking performance as compared, for example, with a plastic plate as thin as the metal plate. The first surface can thus be thin so that the distance between the light emitter and the light receiver can be readily shortened, and the direct light from the light emitter to the light receiver can be effectively blocked or otherwise eliminated.

In the aspect of the invention, the second surface and the third surface may be made of a plastic material.

The second surface and the third surface of the light blocking member can thus be formed, for example, to be lightweight. Further, the second surface and the third surface can each be readily formed, for example, in a complicated shape as compared with a case where the second surface and the third surface are made of a metal material.

In the aspect of the invention, the second surface and the third surface may be formed by shaping the plastic material in injection molding.

With this configuration, volume producibility of the second surface and the third surface of the light blocking member can be improved or otherwise increased (second and third surfaces can be more readily manufactured). Specifically, when the second surface and the third surface are formed in injection molding, a die can be used to form or otherwise produce a second surface and a third surface each having a complicated shape readily and uniformly (with individual variation suppressed). Further, for example, the enclosure of the light detection unit and the second and third surfaces can be integrally molded. In this case, the light detection unit can, for example, be manufactured at a reduced cost.

In the aspect of the invention, the second material may be a metal material, and the first material may be a material other than the metal material.

Therefore, for example, the second surface and the third surface of the light blocking member can be made of a metal material, and the first surface can be made of a material other than the metal material. In particular, when a large amount of light is incident into the light receiver from the sides where the second surface and the third surface are present, light incident into the light receiver can be effectively blocked or otherwise eliminated than the case where each of the second surface and the third surface is formed of a plastic plate. Further, when the enclosure of the light detection unit is made of a metal, the enclosure and the second and third surfaces can be integrally molded, whereby the light detection unit can, for example, be manufactured at a reduced cost.

In the aspect of the invention, each of the second surface and the third surface may be a metal plate formed in sheet metal working.

With this configuration, the second surface and the third surface are made thin to reduce the size of the light detection unit, and the light incident on the light receiver from the sides where the second surface and the third surface are present can be effectively blocked or otherwise eliminated.

Another aspect of the invention relates to a light detection unit including a light emitter that emits light toward an object of interest, a light receiver that receives light from the object of interest, and a light blocking member that performs light blocking at least on the light receiver. The light blocking member includes a first surface that is provided between the light emitter and the light receiver and prevents direct light from the light emitter from entering the light receiver and a second surface and a third surface that are provided along a direction that intersects the first surface and prevent light from entering the light receiver. Each of the second surface and the third surface is a metal plate formed in sheet metal working, and the first surface is a metal plate formed separately from the second surface and the third surface.

With this configuration, for example, the first surface, the second surface, and the third surface can be sheet metals having the same shape, for example, for further reduction in the manufacturing cost of the light blocking member. Further, the first surface can be made thin to readily shorten the distance between the light emitter and the light receiver with the direct light from the light emitter to the light receiver effectively blocked or otherwise eliminated. Moreover, the second surface and the third surface can be made thin to reduce the size of the light detection unit, and the light incident on the light receiver from the sides where the second surface and the third surface are present can be effectively blocked or otherwise eliminated.

In the aspect of the invention, in a front view in which the first surface is viewed from the side where the light emitter is present, a first end surface of the first surface may protrude toward one side beyond an end surface of the second surface, and in the front view, a second end surface of the first surface that faces away from the first end surface may protrude toward the other side different from the one side beyond an end surface of the third surface.

The protruding first and second end surfaces of the first surface therefore block the light from the light emitter, whereby, for example, a situation in which the light from the light emitter undesirably enters the light receiver can be avoided.

In the aspect of the invention, the first surface and the second surface may be so provided that they are adjacent to each other with a first gap area therebetween, and the first surface and the third surface may be so provided that they are adjacent to each other with a second gap area therebetween.

When the first surface, the second surface, and the third surface are assembled to each other, an assembly error may undesirably cause formation of the first gap area and the second gap area. Even in this case, the protruding first and second end surfaces of the first surface block the light from the light emitter, whereby, for example, a situation in which the light from the light emitter undesirably enters the light receiver can be avoided.

In the aspect of the invention, the light blocking member may further have a fourth surface that is provided along a direction that intersects the first surface and prevents light from entering the light receiver, and a diaphragm that narrows light from the object of interest along the optical path between the object of interest and the light receiver may be formed in the fourth surface.

With this configuration, stray light from the object of interest or the like is not allowed to enter the light receiver, whereby, for example, the detection performance of the light detection unit can be improved.

In the aspect of the invention, the distance between the light emitter and the light receiver, which is now called a distance LD, may satisfy LD<3 mm.

With this configuration, the distance between the light emitter and the light receiver can be shortened, as compared with the distance in a light detection unit of related art, whereby the sensitivity and other types of detection performance of the light detection unit can be improved.

In the aspect of the invention, 0.3 mm<LD<2.5 mm may be satisfied.

With this configuration, the distance between the light emitter and the light receiver can be further shortened, whereby, for example, the sensitivity and other types of detectivity can be improved. Further, when 0.3 mm<LD is satisfied, for example, a situation in which the detection signal undesirably has insufficient signal strength when no object of interest is present within a range over which the light detection unit can perform measurement can be avoided.

In the aspect of the invention, a substrate on which the light emitter, the light receiver, and the light blocking member are mounted may be further provided. The light blocking member may have a first protrusion and a second protrusion that are locked in holes in the substrate so that the light blocking member is fixed to the substrate. The first protrusion and the second protrusion may be positioned in a non-line-symmetric manner with respect to the center line of the light blocking member.

The protrusions avoid a situation in which the light blocking member is attached to the substrate in a wrong position in a wrong orientation, whereby the assembly of the light detection unit can, for example, be simplified and performed efficiently.

Still another aspect of the invention relates to a biological information detection apparatus including the light detection unit.

BRIEF DESCRIPTION OF DRAWINGS

The invention will be described with reference to the accompanying drawings, wherein like numbers reference like elements.

FIG. 1 is a perspective view showing an example of the configuration of a light detection unit according to an embodiment of the invention.

FIG. 2A is a plan view of the example of the configuration of the light detection unit according to the present embodiment, respectively.

FIG. 2B is a side view of the example of the configuration of the light detection unit according to the present embodiment, respectively.

FIG. 3 includes a plan view, side views, a front view, and a rear view showing the shape of a light blocking member in detail.

FIG. 4 shows the relationship between the distance between a light emitter and a light receiver and a signal strength of a detection signal.

FIG. 5 describes the relationship between the distance between the light emitter and the light receiver and a measurement distance in the depth direction.

FIG. 6A shows an exterior appearance of a biological information detection apparatus according to the present embodiment.

FIG. 6B shows an exterior appearance of a biological information detection apparatus according to the present embodiment.

FIG. 7 shows an exterior appearance of the biological information detection apparatus according to the present embodiment.

FIG. 8 describes how the biological information detection apparatus is worn and communication between the biological information detection apparatus and a terminal apparatus.

FIG. 9 is a functional block diagram of the biological information detection apparatus.

FIG. 10A describes a sensor section.

FIG. 10B describes a sensor section.

DESCRIPTION OF EMBODIMENTS

An embodiment of the invention will be described below. It is noted that the present embodiment, which will be described below, is not intended to unduly limit the contents of the invention set forth in the appended claims. Further, all configurations described in the present embodiment are not necessarily essential configuration requirements of the invention.

1. Light Detection Unit

FIG. 1 is a perspective view showing an example of the configuration of a light detection unit according to the present embodiment, and FIGS. 2A and 2B are a plan view and a side view, respectively.

The light detection unit according to the present embodiment includes a light receiver 140, a light emitter 150, and a light blocking member 70. The light detection unit can further include a substrate 160.

The light emitter 150 emits light toward an object of interest (such as subject), and the light receiver 140 receives light from the object of interest. For example, when the light emitter 150 emits light and the light is reflected off the object of interest, the light receiver 140 receives the reflected light. The light receiver 140 can be achieved, for example, by using a photodiode or any other light receiving device. The light emitter 150 can be achieved, for example, by using an LED or any other light emitting device. For example, the light receiver 140 can be achieved by using a PN-junction diode device or the like formed on a semiconductor substrate. In this case, an angle limiting filter that narrows a light reception angle or a wavelength limiting filter that limits the wavelength range of light incident on the light receiving device may be formed on the diode device.

Consider a case where the light detection unit is used in a pulse rate meter or any other biological information detection apparatus by way of example. The light from the light emitter 150 travels through the interior of a subject that is an object of interest and is diffused or scattered at the epidermis, derma, subcutaneous tissue, and other sites. The light then reaches a blood vessel (site under detection) and is reflected off the blood vessel. In this process, part of the light is absorbed by the blood vessel. Since the pulse affects the blood vessel in such a way that the optical absorptance thereof changes and the amount of reflected light also changes, causing the light receiver 140 to receive the reflected light and detect a change in the amount of received light allows detection of the pulse rate and other types of biological information.

A dome-shaped lens 151 (collector lens in a broad sense) provided on the light emitter 150 is a lens for collecting light from an LED chip (light emitting device chip in a broad sense) sealed in a resin (sealed in light transmissive resin) in the light emitter 150. That is, in the light emitter 150, which is a surface mount device, the LED chip is disposed below the dome-shaped lens 151, and the light from the LED chip is collected by the dome-shaped lens 151 and exits therethrough toward the object of interest. The light detection unit can thus have improved optical efficiency.

The light blocking member 70 is a member for performing light blocking. In FIG. 1, for example, the light blocking member 70 performs light blocking on or above the light receiver 140. That is, the light blocking member 70 is not provided in the area where the light emitter 150 is disposed but is provided in the area where the light receiver 140 is disposed. For example, the light blocking member 70 is so provided that it covers the light receiver 140 and blocks light incident into the light receiver 140 but does not perform light blocking on the light emitter 150. As a variation, the light blocking member 70 can instead be provided in the area where light emitter 150 is disposed.

At least the inner surface of the light blocking member 70 desirably undergoes an anti-reflection treatment. For example, a surface (such as inner surface) of the light blocking member 70 is colored in black or any other predetermined color to prevent irregular reflection of light. The surface of the light blocking member 70 may instead have a moth-eye structure. For example, a structure having protrusions and indentations formed at intervals ranging from several tens to several hundreds of nanometers is formed on the surface of the light blocking member 70 to form an anti-reflection structure. Any of the anti-reflection treatments described above effectively avoids, for example, a situation in which light reflected off the surface of the light blocking member 70 forms stray light that undesirably produces noise components of a detection signal.

The light receiver 140, the light emitter 150, and the light blocking member 70 are mounted on the substrate 160. The substrate 160 is, for example, a rigid substrate. The substrate 160 is provided with terminals 162, which are connected to signal and power-supply terminals 142 of the light receiver 140, and terminals 164, which are connected to and from an external main substrate for signal communication and power supply. For example, the terminals 142 of the light receiver 140 and the terminals 162 on the substrate 160 are connected to each other in a wire bonding process or any other process.

In the present embodiment, the light blocking member 70 has a light blocking wall 100 provided between the light emitter 150 and the light receiver 140. The light blocking wall 100 prevents the light from the light emitter 150 (such as direct light) from entering the light receiver 140. The light blocking wall 100 is formed of a first surface 71 of the light blocking member 70, which is formed, for example, in sheet metal working. That is, the first surface 71, which forms the light blocking wall 100, is provided between the light receiver 140 and the light emitter 150 and prevents the light from the light emitter 150 from entering the light receiver 140.

The light blocking member 70 further has a second surface 72 and a third surface 73. The second and third surfaces 72, 73 are provided along a direction that intersects the first surface 71 (direction perpendicular to first surface, for example). For example, when the first surface 71 is a front surface, the second and third surfaces 72, 73 are side surfaces and form side light blocking walls.

The light from the light emitter 150 (direct light) is therefore not allowed to enter the light receiver 140 for improvement in detection performance.

The first surface 71 is made of a first material, and the second surface 72 and the third surface 73 are made of a second material different from the first material.

Therefore, the first surface 71, which is preferably formed to be thin as will be described later in detail, can be made of a first material that allows formation of a thin surface, and the second surface 72 and the third surface 73, which do not need to be formed to be as thin as the first surface 71, can be made of a second material that is highly suitable for volume production. That is, each of the surfaces that form the light blocking member 70 can be made of an optimum material.

For example, the first material is a metal material, and the second material is a material other than the metal material.

The first surface 71 can therefore be so formed that it is, for example, thinner than the second surface 72 and the third surface 73 while ensuring the strength and other factors of the light blocking member. As a result, the distance between the light emitter 150 and the light receiver 140 can be readily shortened so that the detection performance and the like of the light detection unit can be improved with the light from the light emitter 150 not allowed to enter the light receiver 140.

The second surface 72 and the third surface 73 can, for example, instead be directly formed of an enclosure of the light detection unit (for example, a case section 30, which will be described later with reference to FIGS. 6A and 6B) or formed of any other part that forms the light detection unit. The second surface 72 and the third surface 73 can thus, for example, be manufactured at a reduced cost.

More specifically, the first surface 71 is a metal plate formed in sheet metal working.

The sheet metal working used herein is, for example, a process of machining, cutting, slotting, or bending a metal plate produced, for example, by allowing a metal material to pass through rollers that compress the metal material and reduce the thickness thereof (by drawing the metal material).

The thus manufactured metal plate excels in light blocking performance as compared, for example, with a plastic plate as thin as the metal plate. The first surface 71 can thus be thin so that the distance between the light emitter 150 and the light receiver 140 can be readily shortened, and the direct light from the light emitter 150 to the light receiver 140 can be effectively blocked or otherwise eliminated.

On the other hand, the second surface 72 and the third surface 73 are made of a plastic material.

The second surface 72 and the third surface 73 can thus be formed, for example, to be lightweight. Further, the second surface 72 and the third surface 73 can each be readily formed, for example, in a complicated shape as compared with a case where the second surface 72 and the third surface 73 are made of a metal material.

In this case, the second surface and the third surface are formed by shaping a plastic material in injection molding.

As a result, volume producibility of the second surface and the third surface of the light blocking member can be improved or otherwise increased (second and third surfaces can be more readily manufactured). Specifically, when the second surface 72 and the third surface 73 are formed in injection molding, a die can be used to form or otherwise produce a second surface 72 and a third surface 73 each having a complicated shape readily and uniformly (with individual variation suppressed). Further, for example, the enclosure of the light detection unit and the second and third surfaces 72, 73 can be integrally molded. In this case, the light detection unit can, for example, be manufactured at a reduced cost.

As described above, the first surface 71, which is preferably formed to be thin, can be formed in sheet metal working, and the second surface 72 and the third surface 73, which do not need to be formed to be as thin as the first surface 71, can be made of a plastic material. As a result, the size of the light detection unit can be reduced and the manufacturability of the light detection unit can be improved with the optical performance thereof ensured.

As the material other than the metal material, a rubber material or any other resin material (including natural resin material and synthetic resin material) may be used. That is, the first surface 71 may be formed of a metal plate, and the second surface 72 and the third surface 73 may be made of a rubber material or any other resin material.

In a front view in which the first surface 71 is viewed from the side where the light emitter 150 is present, a first end surface (left end surface) that is one end surface of the first surface 71 and labeled with D1 protrudes toward one side (leftward) beyond an end surface of the second surface 72 that is labeled with D3, as shown in FIGS. 1 and 2A. On the other hand, in the front view described above, a second end surface (right end surface) that is the other end surface of the first surface 71 that faces away from the first end surface and is labeled with D2 protrudes toward the other side (rightward) different from the one side beyond an end surface of the third surface 73 that is labeled with D4. That is, the end surfaces of the first surface 71 that are labeled with D1 and D2 protrude in opposite directions beyond the end surfaces of the second and third surfaces that are labeled with D3 and D4.

For example, the first surface 71 and the second surface 72 are so provided that they are adjacent to each other with a first gap area labeled with E1 in FIG. 2B therebetween. Further, the first surface 71 and the third surface 73 are so provided that they are adjacent to each other with a second gap area therebetween. That is, the rear surface of the first surface 71 and the end surfaces of the second and third surfaces that are labeled with D3 and D4 are not in contact with each other, and the gap areas are present between the rear surface and the end surfaces.

The presence of the gap areas described above can undesirably allow the light from the light emitter 150 to enter the light receiver 140 through the gap areas, as will be described later in detail. In the present embodiment, however, since the end surfaces of the first surface 71 that are labeled with D1 and D2 protrude in opposite directions in the front view beyond the second and third surfaces 72, 73 as described above, the situation in which the light from the light emitter 150 undesirably enters the light receiver 140 can be effectively avoided.

The light blocking member 70 further has a fourth surface 74, which is provided along a direction that intersects the first surface 71 (in direction perpendicular to first surface, for example) and prevents light from entering the light receiver 140. The fourth surface 74 is, for example, the upper surface of the light blocking member 70.

The fourth surface 74 has a diaphragm 80 formed therein, and the diaphragm 80 narrows light from an object of interest (such as reflected light) along the optical path between the object of interest and the light receiver 140. That is, an opening 81 of the diaphragm 80 is formed in the fourth surface 74. The light blocking member 70 still further has a fifth surface 75, which forms a rear light blocking wall and blocks light incident from the rear side.

2. Light Blocking Member 2.1 Sheet Metal Working

In the light detection unit according to the present embodiment, the light blocking member 70 for preventing external light from entering the light receiver 140 and other components is provided, as shown in FIG. 1. The light blocking member 70, specifically, the first surface 71, for example, provides the light blocking wall 100. Further, the light blocking member 70, specifically, the fourth surface 74, for example, provides the diaphragm 80 having the opening 81. The light blocking wall 100 has a wall surface that extends, for example, along a direction that intersects (is perpendicular to) a line segment that connects the center of the light receiver 140 to the center of the light emitter 150. Providing the thus configured light blocking wall 100 prevents the light from the light emitter 150 (direct light) from entering the light receiver 140, whereby the reliability and other factors of detected data can be improved.

That is, as will be described later in detail, the shorter the distance between the light emitter 150 and the light receiver 140, the more the optical efficiency and performance of the light detection unit improves. The optical efficiency and performance, for example, decrease in inversely proportional to the square of the distance. It is therefore desirable that the distance between the light emitter 150 and the light receiver 140 is minimized.

On the other hand, when the distance between the light emitter 150 and the light receiver 140 is shortened, the direct light from the light emitter 150 undesirably enters the light receiver 140, resulting, for example, in an increase in a DC component and hence a decrease in performance. To avoid the situation, in the light detection unit according to the present embodiment, the light blocking wall 100 is provided between the light receiver 140 and the light emitter 150.

For example, FIG. 3 includes a plan view, side views, a front view, and a rear view showing the shape of the light blocking member 70 in detail. In the present embodiment, the first surface 71 of the light blocking member 70 is formed by shaping a metal material in sheet metal working, and the second surface 72 and the third surface 73 are formed by shaping a plastic material in injection molding, as described above. Specifically, the second surface 72, the third surface 73, the fourth surface 74, and the fifth surface 75 are integrally molded by shaping a plastic material in injection molding, and a sheet metal that forms the first surface 71 is assembled to a plastic part formed of the thus integrally molded four surfaces (72 to 75). The light blocking member 70 is thus formed.

The first surface 71, which faces the light emitter 150 in FIG. 1, then forms the light blocking wall 100, which prevents the direct light from the light emitter 150 from entering the light receiver 140. Further, the diaphragm 80, which narrows light from an object of interest along the optical path between the object of interest and the light receiver 140, is formed in the fourth surface 74, which forms the upper surface. That is, the diaphragm 80 having the opening 81 is formed in the fourth surface 74.

As described above, when the first surface 71 formed in sheet metal working is used to provide the light blocking wall 100, the thickness of the light blocking wall 100 can be reduced as compared with a case where the first surface 71 is made of a plastic material. For example, when the first surface 71 is formed in sheet metal working, and even when the thickness of the first surface 71 is, for example, as thin as about 0.1 mm, the resultant light blocking member 70 can have sufficient strength. The thickness of the first surface 71, which forms the light blocking wall 100, can therefore, for example, be about 0.1 mm. The light blocking wall 100 can therefore be sufficiently thin as compared with an approach using injection molding that causes the thickness of the light blocking wall 100 to be undesirably, for example, 0.4 mm or greater, whereby the distance between the light emitter 150 and the light receiver 140 can be shortened accordingly. The length of the optical path of the light from the light emitter 150 to the light receiver 140 via an object of interest can therefore be shortened while the light blocking wall 100 prevents the direct light from the light emitter 150 from entering the light receiver 140, whereby detection performance and the like of the light detection unit can be improved.

The light emitter 150 particularly shown in FIG. 1 is a chip-package-type light emitter. In the chip-package-type light emitter 150, for example, the dome-shaped lens 151 disposed above the LED chip allows the light to exit toward an object of interest at increased efficiency, whereby the detection sensitivity of the light detection unit can be increased.

The chip-package-type light emitter 150, however, undesirably requires a larger footprint when it is mounted, for example, than a light emitter having an LED chip disposed on a reflector. The distance between the light emitter 150 and the light receiver 140 therefore undesirably increases accordingly. In this regard, according to the present embodiment, in which the thickness of the light blocking wall 100 can be sufficiently thin as described above, even when the chip-package-type light emitter 150 is used, the problem described above can be solved, whereby the sensitivity and other types of detection performance of the light detection unit can be improved.

In FIGS. 1 to 2B, the light blocking member 70 is not provided in the area where the light emitter 150 is disposed but is provided only in the area where the light receiver 140 is disposed. That is, the light blocking member 70 covers the light receiver 140 to perform light blocking on the light receiver 140 but does not cover the light emitter 150.

For example, when the light blocking member 70 is so shaped that it also performs light blocking on the light emitter 150, part of the light from the light emitter 150 toward an object of interest is blocked by the light blocking member 70, possibly resulting undesirably, for example, in a decrease in the amount of light with which the object of interest is irradiated and hence a decrease in the sensitivity and other types of detection performance.

In this regard, when the light blocking member 70 is so shaped that it performs light blocking only on the light receiver 140 as shown in FIGS. 1 to 2B, the situation in which the light emitted from the light emitter 150 is blocked by the light blocking member 70 and the amount of light toward the object of interest undesirably decreases can be avoided.

Further, the configuration in which the light blocking member 70 is not provided in the area where light emitter 150 is disposed but is provided only in the area where the light receiver 140 is disposed is advantageous also from a viewpoint of reduction in the thickness of the light detection unit. For example, as shown in FIG. 2B, the light emitter 150 having the dome-shaped lens 151 has a height greater than the height of the light receiver 140 accordingly. Providing the light blocking member 70 in the area where the light emitter 150 is disposed therefore causes the height of the light blocking member 70 in the area where the light emitter 150 is disposed to be increased accordingly, preventing reduction in the thickness of the light detection unit.

In this regard, in the configuration in which the light blocking member 70 is provided only in the area where the light receiver 140 is disposed, no light blocking member 70 is present in the area where the light emitter 150 is disposed, whereby the height of the light blocking member 70 in the area where the light receiver 140 is disposed can be flush with the height of the light emitter 150 side, as shown, for example, in FIG. 2B. The height of the overall light detection unit can therefore be lowered as compared with the approach in which the light blocking member 70 is also provided in the area where the light emitter 150 is disposed, whereby the thickness of the light detection unit can be readily reduced.

Further, the diaphragm 80 is provided in the light blocking member 70, as described above. That is, the opening 81 is formed in the fourth surface 74 or the upper surface of the light blocking member 70, and the opening 81 provides the diaphragm 80. In this case, the open area of the opening 81 in the diaphragm 80 increases with distance toward the light emitter 150. For example, the opening 81 has a semicircular (substantially semicircular) shape, and the portion corresponding to the diameter of the semicircle faces the light emitter 150. The thus shaped opening 81 in the diaphragm 80 allows the light emitted from the light emitter 150 and reflected off an object of interest to efficiently enter the light receiver 140, whereby the sensitivity and other types of detection performance can be improved. The diaphragm 80 will be described later in detail.

However, unlike the example described above, even when the thickness of the first surface 71 is, for example, greater than or equal to 0.4 mm, the optical performance can be ensured. In a case where the second surface 72 and the third surface 73 need to be thin in order to reduce the size of the light detection unit, a case where light incident on the light receiver 140 from the sides where the second surface 72 and the third surface 73 are present needs to be more effectively blocked, or other cases, the second material may be a metal material, and the first material may be a material other than the metal material.

Therefore, for example, the second surface 72 and the third surface 73 can be made of a metal material, and the first surface 71 can be made of a material other than the metal material. In particular, when a large amount of light is incident on the light receiver 140 from the sides where the second surface 72 and the third surface 73 are present, light incident on the light receiver 140 can be effectively blocked or otherwise eliminated than the case where each of the second surface 72 and the third surface 73 is formed of a plastic plate. Further, when the enclosure of the light detection unit is made of a metal, the enclosure and the second and third surfaces 72, 73 can be integrally molded, whereby the light detection unit can, for example, be manufactured at a reduced cost.

In this case, each of the second surface 72 and the third surface 73 may be a metal plate formed in sheet metal working. On the other hand, the first surface 71 may be formed by shaping a plastic material in injection molding.

As a result, the second surface 72 and the third surface 73 are made thin to reduce the size of the light detection unit, and the light incident on the light receiver 140 from the sides where the second surface 72 and the third surface 73 are present can be effectively blocked or otherwise eliminated.

Further, unlike the example described above, each of the second surface 72 and the third surface 73 may be a metal plate formed in sheet metal working, and the first surface 71 may be a metal plate formed separately from the second surface 72 and the third surface 73. That is, the first surface 71, the second surface 72, and the third surface 73 are all metal plates formed separately from each other, and the first surface 71 may be assembled to the second surface 72 and the third surface 73 to form the light blocking member 70.

Therefore, for example, the first surface 71, the second surface 72, and the third surface 73 can be sheet metals having the same shape, for example, for further reduction in the manufacturing cost. Further, the first surface 71 can be made thin to readily shorten the distance between the light emitter 150 and the light receiver 140 with the direct light from the light emitter 150 to the light receiver 140 effectively blocked or otherwise eliminated. Moreover, the second surface 72 and the third surface 73 can be made thin to reduce the size of the light detection unit, and the light incident on the light receiver 140 from the sides where the second surface 72 and the third surface 73 are present can be effectively blocked or otherwise eliminated.

2.2 Gap Areas

When the first surface 71 is assembled to the second surface 72 and the third surface 73 to form the light blocking member 70 as described above, an assembly error undesirably causes formation of a gap area between the first surface 71 and the second surface 72 adjacent to each other in some cases, as indicated by E1 shown in FIG. 3. Similarly, a gap area is undesirably formed between the first surface 71 and the third surface 73 adjacent to each other in some cases, as indicated by E2. Further, gap areas are undesirably formed between the fifth surface 75 and the second surface 72 and between the fifth surface 75 and the third surface 73, respectively, in some cases, as indicated by E3 and E4.

When the gap areas labeled with E1 and E2 are formed, for example, the light from the light emitter 150 undesirably passes through the gap areas and enters the light receiver 140, possibly resulting undesirably in an increase in a DC component and the like due to the direct light and hence a decrease in the performance.

To avoid the situation, in the present embodiment, the light blocking member 70 is so formed that in a front view in which the light blocking member 70 is viewed from the side where the light emitter 150 is present (front view in direction perpendicular to surface 71), the end surfaces of the first surface 71 that are labeled with D1 and D2 in FIG. 3 protrude in opposite directions beyond the end surfaces of the second and third surfaces 72, 73 that are labeled with D3 and D4. For example, the end surface of the first surface 71 that is labeled with D1 protrudes leftward (toward one side) beyond the end surface of the second surface 72 that is labeled with D3, and the end surface of the first surface 71 that is labeled with D2 protrudes rightward (toward other side) beyond the end surface of the third surface 73 that is labeled with D4. That is, the first surface 71 has protruding portions that extend therefrom and are labeled with F1 and F2 in FIG. 3.

In this configuration, even when the gap areas labeled with E1 and E2 are formed, the direct light from the light emitter 150 is blocked by the protruding portions of the first surface 71 that are labeled with F1 and F2 and is not allowed to enter the light receiver 140. That is, external light other than the direct light may possibly enter through the gap areas, but at least the direct light from the light emitter 150 is blocked by the protruding portions of the first surface 71 and is not allowed to enter the light receiver 140.

Therefore, the direct light incident on the light receiver due to the presence of the gap areas at the boundaries between the sides of the surfaces of the light blocking member can be so suppressed that the detection performance does not lower.

The positional relationship between the end surfaces of the first surface 71 that are labeled with D1 and D2 and the end surfaces of the second and third surfaces 72, 73 that are labeled with D3 and D4 and the shapes and other factors of the end surfaces are not limited to the positional relationship, the shapes, and other factors shown in FIG. 3. That is, a variety of variations are conceivable as long as the positional relationship and the shapes are so set that the first surface 71 has at least the protruding portions that extend therefrom and cover the end surfaces labeled with D3 and D4 as indicated by F1 and F2 and the light from the light emitter 150 is blocked by the protruding portions.

Further, the light emitter 150, the light receiver 140, and the light blocking member 70 are mounted on the substrate 160, as shown in FIG. 1 described above. The light blocking member 70 has protrusions 78 and 79 (first and second protrusions), as shown in FIG. 3. That is, the light blocking member 70 has the protrusions 78 and 79 for fixing the light blocking member 70 to the substrate 160. The protrusions 78 and 79 are locked in holes formed in the substrate 160. The light blocking member 70 is thus fixed to the substrate 160.

Specifically, in FIG. 3, the protrusion 78 is formed on the fifth surface 75, which is the rear surface, and the protrusion 79 is formed on the third surface 73, which is the right side surface. In this case, the positions and shapes of the protrusions 78 and 79 are not set in a line symmetry manner with respect to a center line CL of the light blocking member 70 but set in a non-line-symmetric manner. For example, the protrusions 78 and 79 are not positioned in a line symmetric manner with respect to the center line CL but are positioned in a non-line-symmetric manner. The center line CL corresponds, for example, to a line that connects the center of the light receiver 140 to the center of the light emitter 150. Further, the surfaces of the protrusions 78 and 79 are also not oriented in a line symmetric manner with respect to the center line CL. For example, the surface of the protrusion 78 extends along a direction perpendicular to the center line, and the protrusion 79 has a surface extending along the direction of the center line.

As described above, non-line-symmetric positions and shapes of the protrusions 78 and 79 avoid a situation in which the light blocking member 70 is attached to the substrate 160 in a wrong position in a wrong orientation. The assembly of the light detection unit can therefore be simplified and performed efficiently, whereby cost reduction and other advantages are achieved. That is, forming the protrusion 78, for example, in a left portion of the fifth surface 75, which is the rear surface, and forming the protrusion 79, for example, in a front portion of the third surface 73, which is the right side surface, as shown in FIG. 3 can provide the protrusions 78 and 79 positioned and shaped in a non-line-symmetric manner.

2.3 Distance Between Light Emitter and Light Receiver

FIG. 4 shows the relationship between the distance LD between the light emitter 150 and the light receiver 140 and a signal strength. The signal strength is the strength of a detection signal from a detection apparatus in which the light detection unit according to the present embodiment is used. When the light detection unit is used, for example, in a detection apparatus that will be described later for detecting biological information, such as a pulse wave, the signal strength is the strength of a biological information detection signal, such as a pulse wave detection signal. Further, the distance LD between the light emitter 150 and the light receiver 140 is, for example, the distance between the centers (representative positions) of the light emitter 150 and the light receiver 140. For example, when the light receiver 140 has a rectangular shape (substantially rectangular shape), the position of the light receiver 140 is the center of the rectangular shape. Further, when the light emitter 150 has the dome-shaped lens 151 described above, the position of the light emitter 150 is, for example, the center of the dome-shaped lens 151 (position of LED chip).

As clearly shown in FIG. 4, the smaller the distance LD between the light emitter 150 and the light receiver 140, the greater the signal strength of the detection signal, whereby the sensitivity and other types of detection performance are improved. The distance LD between the light emitter 150 and the light receiver 140 is therefore desirably minimized.

In this regard, in the present embodiment, the first surface 71 of the light blocking member 70 is formed by shaping a metal in sheet metal working, and the first surface 71 provides the light blocking wall 100, as shown in FIGS. 1 to 3 described above. The thickness of the light blocking wall 100 can therefore be thinner than in a case where the light blocking member 70 is formed in injection molding and can, for example, be about 0.1 mm. The distance LD between the light emitter 150 and the light receiver 140 can therefore be shortened by the amount of reduction in the thickness of the light blocking wall 100, whereby the detection performance of the detection apparatus can be improved, as clearly shown in FIG. 4.

In this case, the distance between the light receiver 140 and the light emitter 150 desirably satisfies that LD<3 mm, as shown in FIG. 4. As clearly indicated, for example, by a tangential line G2, which is tangential to a characteristic line G1 and present in a long-distance range in FIG. 4, the characteristic line G1 is saturated in the range of LD>=3 mm. In contrast, in the range of LD<3 mm, signal strength greatly increases as the distance LD decreases. In this sense, it is desirable to satisfy LD<3 mm.

The distance LD further desirably satisfies LD<2.5 mm. For example, as one can see based on the relationship between the tangential line G2 in a long-distance range in FIG. 4 and a tangential line G3 in a short-distance range, in the range where the distance LD is smaller than 2.5 mm (2.4 mm), the rate of increase in the signal strength versus the distance further increases. In this sense, it is therefore further desirable to satisfy LD<2.5 mm.

In the light detection unit according to the present embodiment shown in FIGS. 1 to 3, the distance LD, for example, satisfies that LD is about 2.0 mm. The detection performance can therefore be greatly improved as compared with a light detection unit of related art in which LD>=3 mm, as shown in FIG. 4.

Further, the distance LD has a lower limit, and it is therefore not desirable to set the distance LD at too small a value. For example, FIG. 5 shows a case where the light detection unit according to the present embodiment is used in a detection apparatus for detecting biological information, such as a pulse wave. In this case, the light from the light emitter 150 is diffused or scattered at a blood vessel or any other site in a subject, and the diffused or scattered light enters the light receiver 140, which then detects a pulse wave. In FIG. 5, the distance LD between the light emitter 150 and the light receiver 140 and a measurement distance LB in the depth direction typically satisfy a relationship of LD=2*LB. A limit of the distance of measurement performed by the light detection unit formed of the light emitter 150 and the light receiver 140 separated from each other, for example, by the distance LD is therefore approximately LB=LD/2. In a range of the distance LB, for example, from 100 to 150 micrometer, no blood vessel that is an object of interest from which a pulse wave is detected is present. Therefore, when the distance LD falls within a range of LD<=2*LB=2*100 micrometer to 2*150 micrometer=0.2 to 0.3 mm, it is expected that the magnitude of a pulse wave detection signal is very small. That is, the shorter the distance LD, the shorter the measurement distance LB in the depth direction accordingly, and when no object to be detected is present within the range of the distance LB, the magnitude of the detection signal is undesirably very small. That is, the shorter the distance LD, the more the detection performance is improved, but the improvement is limited or has a lower limit. In this sense, it is therefore desirable to satisfy LD>0.3 mm. That is, it is therefore desirable to satisfy 0.3 mm<LD<2.5 mm (or 0.3 mm<LD<3.0 mm).

3. Biological Information Detection Apparatus 3.1 Example of Overall Configuration of Biological Information Detection Apparatus FIGS. 6A and 6B and FIG. 7 show exterior appearances of a biological information detection apparatus (biological information measurement apparatus) according to the present embodiment. FIG. 6A shows the biological information detection apparatus viewed from the front, and FIG. 6B shows the biological information detection apparatus viewed from above. FIG. 7 shows the biological information detection apparatus viewed from a side.

The biological information detection apparatus according to the present embodiment includes a band section 10, a case section 30, and a sensor section 40, as shown in FIGS. 6A to 7. The case section 30 is attached to the band section 10. The sensor section 40 is provided in the case section 30. The biological information detection apparatus further includes a processing section 200, as shown in FIG. 9, which will be described later. The processing section 200 is provided in the case section 30 and detects biological information based on a detection signal from the sensor section 40. The biological information detection apparatus according to the present embodiment does not necessarily have the configuration shown in FIGS. 6A to 7, and a variety of variations are conceivable. For example, part of the components in the configuration may be omitted or replaced with other components, or other components may be added to the configuration.

The light detection unit described above is accommodated in the sensor section 40. The sensor section 40 is formed, for example, of the light detection unit including the substrate 160, the light emitter 150, the light receiver 140, the light blocking member 70, and the diaphragm 80 (80-1, 80-2) and other members, as will be described later with reference to FIGS. 10A and 10B. In the example shown in FIG. 10A, the other members include a protruding portion 52, a groove 54, a recessed portion 56, a pressing suppression portion 58, and other portions, each of which is achieved by a light transmissive member 50. It is, however, noted that the light detection unit according to the present embodiment may instead include the other members, that is, the sensor section 40 as a whole may correspond to the light detection unit, or other variations are conceivable.

A user winds the band section 10 around a user's wrist to wear the biological information detection apparatus. The band section 10 includes band holes 12 and a buckle 14. The buckle 14 has a band insertion portion 15 and a protrusion 16. The user inserts one end of the band section 10 into the band insertion portion 15 of the buckle 14 and inserts the protrusion 16 of the buckle 14 into any of the band holes 12 of the band section 10 to wear the biological information detection apparatus around the wrist. In this case, in accordance with the band hole 12 to which the protrusion 16 is inserted among the band holes 12, the magnitude of pressure applied by the sensor section 40, which will be described later, (pressure applied to surface of wrist) is adjusted.

The case section 30 corresponds to a main body of the biological information detection apparatus. Inside the case section 30 are provided the sensor section 40, the processing section 200, and a variety of other components that form the biological information detection apparatus. That is, the case section 30 is an enclosure that accommodates the components described above. The case section 30 has, for example, a top case 34 and a bottom case 36. It is noted that the case section 30 is not necessarily separated into the top case 34 and the bottom case 36.

The case section 30 is provided with a light emission window 32. The light emission window 32 is formed of a light transmissive member. The case section 30 is further provided with a light emitter (LED, light emitter for notification different from light emitter 150 in light detection unit) mounted on a flexible substrate, and light from the light emitter exits out of the case section 30 through the light emission window 32.

The case section 30 is provided with terminals 35, as shown in FIG. 7. When the biological information detection apparatus is placed on a cradle that is not shown, terminals of the cradle are electrically connected to the terminals 35 on the case section 30. A secondary battery provided in the case section 30 can thus be charged.

The sensor section 40 detects biological information of a subject, such as a pulse wave. For example, the sensor section 40 includes the light receiver 140 and the light emitter 150 as shown in FIGS. 9 and 10A, which will be described later. The sensor section 40 further includes the protruding portion 52, which is formed of a light transmissive member and comes into contact with a skin surface of the subject and presses the skin surface. In a state in which the protruding portion 52 presses the skin surface, the light emitter 150 emits light, which is reflected off the subject (blood vessel) and received by the light receiver 140, and a result of the light reception is outputted in the form of a detection signal to the processing section 200. The processing section 200 then detects biological information, such as a pulse wave, based on the detection signal from the sensor section 40. The biological information to be detected by the biological information detection apparatus according to the present embodiment is not limited to a pulse wave (pulse rate), and the biological information detection apparatus may be an apparatus that detects biological information other than a pulse wave (blood oxygen saturation level, body temperature, and heartbeat, for example).

FIG. 8 describes how the biological information detection apparatus 400 is worn and communication between the biological information detection apparatus 400 and a terminal apparatus 420.

The user or a subject wears the biological information detection apparatus 400 around a wrist 410, as the user wears a wristwatch, as shown in FIG. 8. The sensor section 40 is provided on the subject-side surface of the case section 30, as shown in FIG. 7. Therefore, when the user wears the biological information detection apparatus 400, the protruding portion 52 of the sensor section 40 comes into contact with the skin surface of the wrist 410 and presses the skin surface. In this state, the light emitter 150 in the sensor section 40 emits light and the light receiver 140 receives reflected light, whereby biological information, such as a pulse wave, is detected.

The biological information detection apparatus 400 and the terminal apparatus 420 are connected to each other in a communicatable manner so that data can be transferred between them. The terminal apparatus 420 is, for example, a smartphone, a mobile phone, a feature phone, or any other mobile communication terminal. The terminal apparatus 420 may instead be a tablet computer or any other information processing terminal. To connect the biological information detection apparatus 400 and the terminal apparatus 420 to each other in a communicatable manner, for example, Bluetooth (registered trademark) or any other near-range wireless communication can be employed. When the biological information detection apparatus 400 and the terminal apparatus 420 are connected to each other in a communicatable manner as described above, a display section 430 (such as LCD) of the terminal apparatus 420 can display a variety of types of information, such as the pulse rate and calorie consumption. That is, a variety of types of information determined based on the detection signal from the sensor section 40 can be displayed. The information, such as the pulse rate and calorie consumption, may be computed in the biological information detection apparatus 400, or at least part of the information may be computed in the terminal apparatus 420.

The biological information detection apparatus 400 is provided with the light emission window 32, and light emission (lighting, blinking) from the light emitter for notification notifies the user of the variety of types of information. For example, when the heart rate changes and falls within a fat-burning zone or goes out of the zone, the light emission from the light emitter via the light emission window 32 notifies the user of the state of the heart rate. Further, when the terminal apparatus 420 receives a mail message or the like, the terminal apparatus 420 notifies the biological information detection apparatus 400 of the reception. The light emitter in the biological information detection apparatus 400 then emits light to notify the user of the reception of the mail message or the like.

As described above, in FIG. 8, the biological information detection apparatus 400 is provided with no display section, such as an LCD, and the display section 430 of the terminal apparatus 420 displays information necessary to be notified in the form of characters, numerals, or any other objects. As described above, in FIG. 8, the biological information detection apparatus 400 is provided with no display section, such as an LCD, but the light emission from the light emitter notifies the user of requisite minimum information, whereby the size of the biological information detection apparatus 400 is reduced. Further, the aesthetic appearance of the biological information detection apparatus 400 can also be improved because the biological information detection apparatus 400 is provided with no display section.

FIG. 9 is a functional block diagram of the biological information detection apparatus according to the present embodiment. In FIG. 9, the biological information detection apparatus includes the sensor section 40, a body motion sensor section 170, a vibration generation section 180, the processing section 200, a storage section 240, a communication section 250, an antenna 252, and a notification section 260. The biological information detection apparatus according to the present embodiment does not necessarily have the configuration shown in FIG. 9, and a variety of variations are conceivable. For example, part of the components in the configuration may be omitted or replaced with other components, or other components may be added to the configuration.

The sensor section 40 detects biological information, such as a pulse wave, and includes the light receiver 140 and the light emitter 150. The light receiver 140, the light emitter 150, and other components achieve a pulse wave sensor (photoelectric sensor). The sensor section 40 outputs a signal detected with the pulse wave sensor as a pulse wave detection signal.

The body motion sensor section 170 outputs a body motion detection signal, which is a signal that changes in accordance with body motion, based on sensor information from a variety of sensors. The body motion sensor section 170 includes, for example, an acceleration sensor 172 as a body motion sensor. The body motion sensor section 170 may instead include a pressure sensor, a gyro sensor, or any other sensor as the body motion sensor.

The processing section 200 performs a variety of types of signal processing and control processing, for example, by using the storage section 240 as a work area and can be achieved, for example, by a CPU or any other processor or an ASIC or any other logic circuit. The processing section 200 includes a signal processing portion 210, a beating information computing portion 220, and a notification control portion 230.

The signal processing portion 210 performs a variety of types of signal processing (such as filtering) and performs the signal processing, for example, on the pulse wave detection signal from the sensor section 40 and the body motion detection signal from the body motion sensor section 170. For example, the signal processing portion 210 includes a body motion noise reduction portion 212. The body motion noise reduction portion 212 reduces (removes) body motion noise, which is noise resulting from body motion, from the pulse wave detection signal based on the body motion detection signal from the body motion sensor section 170. Specifically, the body motion noise reduction portion 212 performs noise reduction, for example, using an adaptation filter.

The beating information computing portion 220 computes beating information based, for example, on a signal from the signal processing portion 210. The beating information is information, for example, on the pulse rate. Specifically, the beating information computing portion 220 performs FFT or any other type of frequency analysis on the pulse wave detection signal having undergone the noise reduction in the body motion noise reduction portion 212 to determine a spectrum, extracts a representative frequency from the determined spectrum, and sets the extracted frequency as the frequency of the heart beat. The determined frequency multiplied by 60 is the typically used as the pulse rate (heart rate). The beating information is not limited to the pulse rate itself and may, for example, be a variety of other types of information representing the pulse rate (frequency or period of heartbeat, for example). The beating information may still instead be information representing the state of beating. For example, the beating information may be a value directly representing a blood volume.

The notification control portion 230 controls the notification section 260. The notification section 260 (notification device) notifies the user of a variety of types of information under the control of the notification control portion 230. The notification section 260 can, for example, be the light emitter for notification. In this case, the notification control portion 230 controls the current flowing through the LED to control the lighting, blinking, or any other behavior of the light emitter. The notification section 260 may instead, for example, be an LCD or any other display device or a buzzer.

The notification control portion 230 further controls the vibration generation section 180. The vibration generation section 180 notifies the user of a variety of types of information in the form of vibration. The vibration generation section 180 can be achieved, for example, by using a vibration motor (vibrator). The vibration motor produces vibration by rotating a decentered weight. Specifically, a decentered weight is attached to each end of a drive shaft (rotor shaft) of the motor so that the motor itself makes swing motion. The vibration of the vibration generation section 180 is controlled by the notification control portion 230. The vibration generation section 180 is not limited to the vibration motor described above, and a variety of variations are conceivable. The vibration generation section 180 may instead be achieved, for example, by using a piezoelectric device.

The vibration of the vibration generation section 180, for example, allows notification of startup at power-on, notification of successful initial pulse wave detection, an alarm issued when a state in which no pulse wave can be detected lasts for a fixed period, notification of a shift of the heart rate into or out of the fat-burning zone, an alarm issued when the battery voltage decreases, notification of a wakeup alarm, or notification of a mail message, a telephone call, and the like from a smartphone or any other terminal device. The information described above may be notified by using the light emitter for notification or by using both the vibration generation section 180 and the light emitter.

The communication section 250 communicates with the external terminal apparatus 420, as described with reference to FIG. 8. For example, the communication section 250 performs wireless communication that complies, for example, with the Bluetooth (registered trademark) standard. Specifically, the communication section 250 receives a signal from the antenna 252 and transmits a signal to the antenna 252. The functions of the communication section 250 can be achieved by a processor for communication or an ASIC or any other logic circuit.

3.2 Example of Configuration of Sensor Section

FIG. 10A shows an example of the configuration of the sensor section 40 in detail. The sensor section 40 includes the light receiver 140 and the light emitter 150. The light receiver 140 and the light emitter 150 are mounted on the substrate 160 (sensor substrate). The light receiver 140 receives light from a subject (such as reflected light, transmitted light). The light emitter 150 emits light toward the subject. For example, when the light emitter 150 emits light toward the subject and the light is reflected off the subject (blood vessel), the light receiver 140 receives and detects the reflected light. The light receiver 140 can be achieved, for example, by using a photodiode or any other light receiving device. The light emitter 150 can be achieved, for example, by using an LED or any other light emitting device. For example, the light receiver 140 can be achieved by using a PN-junction diode device or the like formed on a semiconductor substrate. In this case, an angle limiting filter that narrows a light reception angle or a wavelength limiting filter that limits the wavelength range of light incident on the light receiving device may be formed on the diode device.

In the case of a pulse rate meter by way of example, the light from the light emitter 150 travels through the interior of a subject and is diffused or scattered at the epidermis, derma, subcutaneous tissue, and other sites. The light then reaches a blood vessel (site under detection) and is reflected off the blood vessel. In this process, part of the light is absorbed by the blood vessel. Since the pulse affects the blood vessel in such a way that the optical absorptance thereof changes and the amount of reflected light also changes, causing the light receiver 140 to receive the reflected light to detect a change in the amount of received light allows detection of the pulse rate and other types of biological information.

The light blocking member 70 (light blocking wall 100) is provided between the light receiver 140 and the light emitter 150. The light blocking member 70, for example, prevents the light from the light emitter 150 from directly entering the light receiver 140.

The sensor section 40 is further provided with the diaphragm 80 (80-1, 80-2). The diaphragm 80 narrows the light from the subject and the light from the light emitter 150 along the optical path between the subject and the sensor section 40. In FIG. 10A, the diaphragm 80 is provided between the light transmissive member 50 and the light emitter 150. The diaphragm 80 may instead be provided between the light transmissive member 50 and the subject or in the light transmissive member 50.

The light transmissive member 50 is provided on a surface of the biological information detection apparatus, specifically, a surface thereof that comes in contact with the subject, and transmits the light from the subject. The light transmissive member 50 comes into contact with the subject when biological information on the subject is measured. For example, the protruding portion 52 (detection window) of the light transmissive member 50 comes into contact with the subject. The surface of the protruding portion 52 desirably, but not necessarily, has a curved shape (spherical shape) and can instead have a variety of shapes. Further, the light transmissive member 50 only needs to be transparent to the wavelength range of the light from the subject and may be made of a transparent material or a colored material.

The groove 54 for suppressing, for example, variation in the pressure is provided around the protruding portion 52 of the light transmissive member 50. Further, assuming that a surface of the light transmissive member 50 on the side where the protruding portion 52 is provided is called a first surface, the light transmissive member 50 has the recessed portion 56 on the side of a second surface facing away from the first surface in a position corresponding to the protruding portion 52. In the space of the recessed portion 56 are provided the light receiver 140, the light emitter 150, the light blocking member 70, and the diaphragm 80.

Further, on the subject-side surface of the biological information detection apparatus is provided the pressure suppression portion 58, which suppresses the pressure exerted by the protruding portion 52 on the subject (wrist skin). In FIG. 10A, the pressure suppression portion 58 is so provided that it surrounds the protruding portion 52 of the light transmissive member 50.

In FIG. 10A, let HA be the height of the protruding portion 52 in the direction perpendicular to the subject-side surface of the biological information detection apparatus (height of vertex of curved shape of protruding portion 52, for example), HB be the height of the pressure suppression portion 58 (height at the highest position, for example), and delta_h be a value obtained by subtracting the height HB from the height HA (difference between height HA and height HB), a relationship of delta_h=HA-HB>0 is satisfied. For example, the protruding portion 52 protrudes beyond the pressure suppression portion 58 toward the subject with delta_h>0 satisfied. That is, the protruding portion 52 protrudes beyond the pressure suppression section (pressure suppression surface) 58 toward the subject by delta_h.

As described above, providing the protruding portion 52 that satisfies delta_h>0, for example, allows initial pressure for achieving a state in which a vein vanishing point is reached and exceeded to be applied to the subject. Further, providing the pressure suppression portion 58 for suppressing the pressure exerted by the protruding portion 52 on the subject can minimize variation in the pressure within a range over which the biological information detection apparatus is used to measure biological information, whereby the amount of noise components and the like can be reduced. Further, when the protruding portion 52 protrudes from the pressure suppression portion 58 in such a way that delta_h> is satisfied, the protruding portion 52 first comes into contact with the subject and exerts the initial pressure, and the pressure suppression portion 58 then comes into contact with the subject to suppress the pressure applied by the protruding portion 52 to the subject. The vein vanishing point used herein is a point where when the protruding portion 52 is pressed against the subject and the pressure is gradually increased, a signal resulting from the vein and superimposed on the pulse wave signal vanishes or lowers to the extent that the signal does not affect the pulse wave measurement.

In FIG. 10B, for example, the horizontal axis represents a load produced by a loading mechanism (mechanism formed, for example, of band section and buckle section) of the biological information detection apparatus, and the vertical axis represents the pressure exerted by the protruding portion 52 on the subject (pressure acting on blood vessel). The amount of change in the pressure exerted by the protruding portion 52 versus the load produced by the loading mechanism that produces the pressure from the protruding portion 52 is now called a pressure change amount. The pressure change amount corresponds to the gradient of a pressure change characteristic curve versus the load.

In this case, the pressure suppression portion 58 suppresses the pressure exerted by the protruding portion 52 on the subject in such a way that, with reference to a pressure change amount VF1 over a first load range RF1 where the load produced by the loading mechanism ranges from 0 to FL1, a pressure change amount VF2 over a second load range RF2 where the load produced by the loading mechanism is greater than FL1 is smaller than the pressure change amount VF1. That is, the pressure change amount VF1 has a large value over the first load range RF1, which is an initial pressure range, whereas the pressure change amount VF2 has a small value over the second load range RF2, which is the range over which the biological information detection apparatus is used.

That is, over the first load range RF1, the pressure change amount VF1 has a large value so that the gradient of the pressure change characteristic curve versus the load has a large value. The pressure corresponding to a large gradient of the change characteristic curve is achieved by delta_h equal to the amount of protrusion of the protruding portion 52. That is, providing the protruding portion 52 that satisfies delta_h>0 allows an initial pressure necessary and sufficient to exceed the vein vanishing point to be applied to the subject even when the load produced by the loading mechanism is small.

On the other hand, over the second load range RF2, the pressure change amount VF2 has a small value so that the gradient of the pressure change characteristic curve versus the load has a small value. The pressure corresponding to a small gradient of the change characteristic curve is achieved by the pressure suppression provided by the pressure suppression portion 58. That is, the pressure suppression portion 58, which suppresses the pressure exerted by the protruding portion 52 on the subject, even when the load varies or otherwise changes within the range over which the biological information detection apparatus is used, can minimize the variation in the pressure. As a result, for example, the amount of noise components can be reduced.

As described above, when an optimized pressure (about 16 kPa, for example) is allowed to be applied to the subject, a pulse wave detection signal having a higher M/N ratio (S/N ratio) can be produced. That is, the signal component from the pulse wave sensor can be increased, and the noise components therefrom can be decreased. In the description, M stands for the signal level of the pulse wave detection signal, and N stands for the noise level.

Further, setting the range of the pressure used for the pulse wave measurement to be a range corresponding to the second load range RF2 allows the variation in the pressure to be minimized (about +/−4 kPa, for example), whereby the amount of noise components can be reduced.

The present embodiment has been described above in detail, and a person skilled in the art will readily appreciate that a large number of variations are conceivable to the extent that they do not substantially depart from the novel items and advantageous effects of the invention. Such variations are all therefore assumed to fall within the scope of the invention. For example, a term described at least once in the specification or the drawings along with a different term having a boarder meaning or the same meaning can be replaced with the different term anywhere in the specification or the drawings. Further, the configuration and operation of each of the light detection unit, the biological information detection apparatus, and other components are not limited to those described in the present embodiment, and a variety of changes can be made thereto.

The invention claimed is:
1. A light detection unit comprising:
a light emitter that emits light toward an object of interest;
a light receiver that receives light from the object of interest; and
a light blocking member that performs light blocking at least above the light receiver,
wherein the light blocking member includes
a first surface that is provided between the light emitter and the light receiver and prevents direct light from the light emitter from entering the light receiver, and
a second surface and a third surface that are provided along a direction that intersects the first surface and prevent light from entering the light receiver,
the first surface is made of a first material,
the second surface and the third surface are made of a second material different from the first material, and the second surface and the third surface are disposed only on a light receiver side of the first surface.

2. The light detection unit according to claim 1, wherein the first material is a metal material and the second material is a material other than the metal material.

3. The light detection unit according to claim 2, wherein the first surface is a metal plate formed in sheet metal working.

4. The light detection unit according to claim 2, wherein the second surface and the third surface are made of a plastic material.

5. The light detection unit according to claim 4, wherein the second surface and the third surface are formed by shaping the plastic material in injection molding.

6. The light detection unit according to claim 1, wherein the second material is a metal material and the first material is a material other than the metal material.

7. The light detection unit according to claim 6, wherein the second surface and the third surface is a metal plate formed in sheet metal working.

8. A light detection unit comprising:
a light emitter that emits light toward an object of interest;
a light receiver that receives light from the object of interest; and
a light blocking member that performs light blocking at least above the light receiver,
wherein the light blocking member includes
a first surface that is provided between the light emitter and the light receiver and prevents direct light from the light emitter from entering the light receiver, and
a second surface and a third surface that are provided along a direction that intersects the first surface and prevent light from entering the light receiver,
each of the second surface and the third surface is a metal plate formed in sheet metal working,
the first surface is a metal plate formed separately from the second surface and the third surface, and
the second surface and the third surface are disposed only on a light receiver side of the first surface.

9. A biological information detection apparatus, comprising:
the light detection unit according to claim 1;
a processing unit that processes a detection signal from the light detection unit to detect the biological information.

10. The light detection unit according to claim 1, a distance LD between the light emitter and the light receiver satisfies 0.3 mm<LD<2.5 mm.

11. The light detection unit according to claim 1, wherein the first surface, the second surface, and the third surface are separate plates that are separated from each other.

12. The light detection unit according to claim 8, wherein the first surface, the second surface, and the third surface are separate metal plates that are separated from each other.

* * * * *